US008088362B2

(12) United States Patent
Church et al.

(10) Patent No.: US 8,088,362 B2
(45) Date of Patent: *Jan. 3, 2012

(54) SALMETEROL SUPERFINE FORMULATION

(75) Inventors: Tanya Kathleen Church, Parma (IT); David Andrew Lewis, Parma (IT); David Ganderton, Parma (IT); Brian John Meakin, Parma (IT); Gaetano Brambilla, Parma (IT)

(73) Assignee: Chiesi Farmaceutici S.p.A., Parma (IT)

(*) Notice: Subject to any disclaimer, the term of this patent is extended or adjusted under 35 U.S.C. 154(b) by 1809 days.

This patent is subject to a terminal disclaimer.

(21) Appl. No.: 10/531,867

(22) PCT Filed: Jun. 18, 2003

(86) PCT No.: PCT/EP03/06444
§ 371 (c)(1), (2), (4) Date: Sep. 16, 2005

(87) PCT Pub. No.: WO2004/037227
PCT Pub. Date: May 6, 2004

(65) Prior Publication Data
US 2006/0120966 A1 Jun. 8, 2006

(30) Foreign Application Priority Data
Oct. 23, 2002 (EP) .................................. 02023589

(51) Int. Cl.
*A61K 9/12* (2006.01)
*A61K 9/00* (2006.01)
(52) U.S. Cl. ........................................................ 424/45
(58) Field of Classification Search .................. 424/45
See application file for complete search history.

(56) References Cited

U.S. PATENT DOCUMENTS

| 5,695,744 | A | * | 12/1997 | Neale et al. ............... 424/45 |
| 6,423,298 | B2 | * | 7/2002 | McNamara et al. .......... 424/45 |
| 6,455,028 | B1 | * | 9/2002 | Wulffhart et al. ........... 424/45 |
| 6,585,958 | B1 | * | 7/2003 | Keller et al. ............... 424/45 |
| 6,713,047 | B1 | | 3/2004 | Lewis et al. |
| 6,716,414 | B2 | | 4/2004 | Lewis et al. |
| 6,964,759 | B2 | | 11/2005 | Lewis et al. |
| 7,018,618 | B2 | | 3/2006 | Lewis et al. |
| 7,074,388 | B2 | * | 7/2006 | Adjei et al. ............... 424/45 |
| 2001/0031244 | A1 | | 10/2001 | Lewis et al. |
| 2002/0189610 | A1 | * | 12/2002 | Bozung et al. ......... 128/200.22 |
| 2003/0066525 | A1 | | 4/2003 | Lewis et al. |
| 2003/0089369 | A1 | | 5/2003 | Lewis et al. |
| 2003/0091512 | A1 | * | 5/2003 | Adjei et al. ............... 424/46 |
| 2003/0190287 | A1 | | 10/2003 | Lewis et al. |
| 2003/0190289 | A1 | | 10/2003 | Lewis et al. |
| 2003/0206870 | A1 | | 11/2003 | Lewis et al. |
| 2004/0062720 | A1 | | 4/2004 | Lewis et al. |
| 2004/0096399 | A1 | | 5/2004 | Lewis et al. |
| 2004/0184993 | A1 | | 9/2004 | Lewis et al. |
| 2005/0048001 | A1 | * | 3/2005 | Cripps et al. ............. 424/45 |
| 2005/0129621 | A1 | | 6/2005 | Davies et al. |
| 2005/0142071 | A1 | | 6/2005 | Lewis et al. |
| 2005/0152846 | A1 | | 7/2005 | Davies et al. |
| 2005/0154013 | A1 | | 7/2005 | Davies et al. |
| 2005/0220718 | A1 | | 10/2005 | Lewis et al. |
| 2006/0057074 | A1 | * | 3/2006 | Meade et al. ............. 424/46 |
| 2006/0120966 | A1 | | 6/2006 | Church et al. |

FOREIGN PATENT DOCUMENTS

| WO | 96 19198 | | 6/1996 |
| WO | WO 96/32151 | * | 10/1996 |
| WO | WO 00/06121 | * | 2/2000 |
| WO | WO 01/47493 | * | 7/2001 |
| WO | 01 78689 | | 10/2001 |
| WO | WO 01/89480 | * | 11/2001 |
| WO | 02 49616 | | 6/2002 |

OTHER PUBLICATIONS

Merriam-Webster's Collegiate Dictionary, 10th edition, Merriam-Webster Incorporated: Springfield, Massachusetts, 1993, pp. 311.*
Vippagunta et al. "Crystalline Solids," Advanced Drug Delivery Reviews, 2001, 48, 1-26.*
Braga et al. Chem. Commun., "Making Crystals from Crystals: a green route to crystal engineering and polymorphism," 2005, pp. 3635-3645.*
Mahler, D. A. et al. "Efficacy of salmeterol xinafoate in the treatment of COPD," CHEST Apr. 1999, 115(4), abstract only.*
Sartori, C. et al. "Salmeterol for the Prevention of High-Altitude Pulmonary Edema," N. Engl. J. Med., May 2002, 346(21), pp. 1631-1636.*
Ware, L. B. and Matthay, M. A., "Alveolar Fluid Clearance is Impaired in the Majority of Patients with Acute Lung Injury and the Acute Respiratory Distress Syndrome," Am J. Respir. Crit. Care Med., 2001, 163, pp. 1376-1383.*
Hordvik, N. L. et al. "Effectiveness and tolerability of high-dose salmeterol in cystic fibrosis," Pediatric Pulmonology, 2002, 34(4), abstract.*
Kips, J. C. and Pauwels, R. A., "Long-acting Inhaled Beta2-Agonist Therapy in Asthma," Am. J. Crit. Car. Med., 2001, 164, pp. 923-932.*
U.S. Appl. No. 11/289,479, filed Nov. 30, 2005, Lewis, et al.
U.S. Appl. No. 09/147,669, filed Feb. 24, 1999, Lewis, et al.
U.S. Appl. No. 09/831,888, filed Jul. 19, 2001, Lewis, et al.
U.S. Appl. No. 10/546,619, filed Aug. 23, 2005, Razzetti, et al.
U.S. Appl. No. 11/408,026, filed Apr. 21, 2006, Lewis, et al.

* cited by examiner

*Primary Examiner* — James H. Alstrum-Acevedo
(74) *Attorney, Agent, or Firm* — Oblon, Spivak, McClelland, Maier & Neustadt, L.L.P.

(57) ABSTRACT

The present invention relates to a pharmaceutical formulation for use in the administration of a long-acting $\beta_2$-agonist by inhalation. In particular this invention relates to a chemically stable, highly efficient salmeterol HFA solution formulation to be administered by pressurized metered dose inhalers (pMDIs) characterized by a deep lung penetration. The invention also relates to methods for the preparation of said formulation and to its use in respiratory diseases such as asthma and chronic obstructive pulmonary disease (COPD).

30 Claims, No Drawings

SALMETEROL SUPERFINE FORMULATION

CROSS REFERENCES TO RELATED APPLICATIONS

This application is a 371 of International Patent Application No. PCT/EP03/06444, filed on Jun. 18, 2003, and claims priority to European Patent Application No. 020235891, filed on Oct. 23, 2002.

The present invention relates to a pharmaceutical formulation for use in the administration of a long-acting $\beta_2$-agonist by inhalation. In particular this invention relates to a chemically stable, highly efficient salmeterol HFA solution formulation to be administered by pressurised metered dose inhalers (pMDIs) characterized by a deep lung penetration.

The invention also relates to methods for the preparation of said formulation and to its use in respiratory diseases such as asthma and chronic obstructive pulmonary disease (COPD).

BACKGROUND OF THE INVENTION

Asthma is a disease which is becoming more prevalent and is the most common disease of childhood. It can be identified by recurrent wheeze and intermittent air flow limitation. Despite many advances in its understanding, said pathology remains a poorly understood and often poorly treated disease. Previously, contraction of airway smooth muscles has been regarded as the most important feature of asthma. Recently there has been a marked change in the way asthma is managed, stemming from the fact that asthma is recognized as a chronic inflammatory disease. Uncontrolled airway inflammation may lead to mucosal damage and structural changes giving irreversible narrowing of the airways and fibrosis of the lung tissue. Therapy should therefore be aimed at controlling symptoms so that normal life is possible and at the same time provide basis for treating the underlying inflammation.

Another respiratory disease whose incidence is steadily increasing throughout the world is chronic obstructive pulmonary disease (COPD). Most patients with COPD have acquired their lung disease through smoking cigarettes. Depending upon trends in tobacco smoking, it is set to rise to fifth most prevalent cause of disability, worldwide by 2020 (Leckie M et al *Exp Opin Invest Drugs* 2000, 9, 3-23).

Chronic obstructive pulmonary disease (COPD) is defined as a disease state characterized by the presence of airflow obstruction due to chronic bronchitis or emphysema.

Chronic bronchitis is characterized by excessive secretion of bronchial mucus, whereas emphysema denotes abnormal, permanent enlargement of air spaces distal to the terminal bronchiole, with destruction of their walls and without obvious fibrosis (American Toracic Society). Each condition is treated as specific diseases.

Chronic obstructive bronchiolitis is due to obstruction of the peripheral airways as a result of inflammation in the bronchioles.

$\beta_2$-Adrenoceptor agonists have been the mainstay of treatment for asthma for many years in view of their prompt bronchodilation effects. Previous researches have also shown that $\beta_2$-agonists have potent anti-inflammatory capabilities, e.g. represented by suppression of release of the pro-inflammatory cytokines.

The first generation drugs such as salbutamol or fenoterol were characterized by a relatively short duration of action which has been considered as a disadvantage particularly for patients with nocturnal asthma. Moreover, they have limited effects in COPD, since this disease involves 'partially irreversible' airways obstruction. The development of longer acting $\beta_2$-agonists such as formoterol, salmeterol and TA 2005 has therefore been heralded as a major new development in the treatment of asthma. According to some authors, long-acting $\beta_2$-agonists (LABAs) may have acute anti-inflammatory activity in vivo (Johnson M *Clin Exp Allergy* 1992, 22, 177-181; Stelmach I et al *Ann Allergy Asthma Immunol* 2002, 89, 67-73). These drugs are a new interesting therapeutic option for patients with chronic obstructive pulmonary disease (COPD) as well since they have been shown to significantly improve lung function and symptom control.

$\beta_2$-adrenergic agonists can also stimulate alveolar fluid clearance in several animal species and in ex vivo rat and human lungs. In view of these findings beta-adrenergic agonist therapy has been proposed as a possible treatment for accelerating the resolution of pulmonary edema in patients with acute pulmonary edema (Sacuma T et al *Am J Respir Crit Care Med* 1997, 155, 506-512). Treatment with $\beta_2$-agonists may also increase the secretion of surfactant and perhaps exert an anti-inflammatory effect, thus helping to restore vascular permeability of the lung (Ware L et al *New Eng. J Med* 2000, 342, 1334-1349.

Drugs intended for the treatment of lung diseases such as asthma and COPD are currently administered by pulmonary delivery which relies on inhalation of an aerosol through the mouth and throat so that the drug substance can reach the lung. They can be administered as aqueous or hydroalcoholic formulations through a nebuliser, as dry powders by means of Dry Powder Inhalers or in halogenated hydrocarbon propellants. The propellant-based systems require suitable pressurized metered-dose inhalers (pMDIs) which release a metered dose of medicine upon each actuation. The relevant formulations can be in the form of solutions or suspensions. Solution formulations, with respect to suspensions, do not present problems of physical stability of the suspended particles and so could guarantee a higher dose uniformity and reproducibility. As far as the type of propellant is concerned, hydrofluoroalkanes [(HFAs) known also as hydro-fluoro-carbons (HFCs)] would be mandatory propellants as chlorofluorocarbons (known also as Freons or CFCs), which were for many years the preferred propellant aerosols for pharmaceutical use, have been implicated in the destruction of the ozone layer so their use is being phased out. In particular, 1,1,1,2-tetrafluoroethane (HFA 134a) and 1,1,1,2,3,3,3-heptafluoropropane (HFA 227) have been acknowledged to be the best candidates for non-CFC propellants and a number of pharmaceutical aerosol formulations using such HFA propellant systems have been disclosed.

In developing a therapeutic aerosol, the aerodynamic size distribution of the inhaled particles is the most important variable in defining the site of droplet or particle deposition in the lungs of the patient; in short, it will determine whether drug targeting succeeds or fails. See P. Byron, "Aerosol Formulation, Generation, and Delivery Using Nonmetered Systems, "Respiratory Drug Delivery, 144-151,144 (CRC Press, 1989).

Thus, a prerequisite in developing a therapeutic aerosol is a preferential particle size.

When the formulation is in the form of suspension, the particle size of the cloud is dominated by the particle size of the suspended drug, defined by the milling/micronization process. When the formulation is in the form of solution, the volumetric contribution of suspended drug particles is absent and much finer liquid droplet clouds, largely defined by the drug concentration in the solution, are generated.

Solid particles and/or droplets in an aerosol formulation can be characterized by their mass median aerodynamic diameter (MMAD, the diameter around which the mass aerodynamic diameters are distributed equally).

Particle deposition in the lung depends largely upon three physical mechanisms:
  i) impaction, a function of particle inertia;
  ii) sedimentation due to gravity; and
  iii) diffusion resulting from Brownian motion of fine, sub-micrometer (<1 microns) particles.

The mass of the particles determines which of the three main mechanisms predominates.

For aerosol therapy of drugs which topically act on the smooth muscle of the conducting airways, and in particular for $\beta_2$-agonists, it has been reported in the past that particles should preferentially deposit in the upper-to mid-pulmonary region (bronchiole region), so they should have a MMAD of about 1.5(2.0) to about 5.0 microns, preferably approximately 3 microns (Zanen P et al Int J Pharm 1994, 107, 211-217; Int J Pharm 1995, 114, 111-115; Thorax, 1996, 51, 977-980).

In fact, particles having aerodynamic diameters of greater than about 5 microns generally do not reach the lung since they tend to impact the back of the throat and are swallowed and possibly orally absorbed, while particles smaller than 1.5 (2.0) micron, i. e., about 0.5 to about 2 microns, capable of reaching the alveolar region, have been considered undesirable because they can be absorbed into the bloodstream and might enhance the undesired systemic effects of the drugs. Particles having diameters smaller than about 0.5 microns have been generally considered as not therapeutically useful as they can be exhaled.

Accordingly, pMDI formulations of $\beta_2$-agonist have traditionally been formulations able to deliver particles whose larger fraction is comprised between 2 and 5 microns and the amount of those below 1 micron is very limited since the former are small enough to reach the upper-to mid-pulmonary region, but are too large to reach the alveoli. This is also the inherent particle size of the formulation in the form of suspensions as conventional micronization (air-jet milling) of pure drug substance can reduce the drug particle size to about 2-3 microns.

On the other hand, it is known that the density of the beta-adrenergic receptors is higher in the distal tract of the bronchioles (Barnes P et al Am Rev Respir Dis 1983, 127, 758-762), a region which is better reached by smaller particles. Moreover inflammation in asthma is not merely confined to the large central airways but also extends to small peripheral airways. The eosinophilic inflammation process which has been seen to be associated to asthma concerns both the bronchial and the alveolar districts (Wang S J Immunol 2001, 166, 2741-2749). Recently, Martin R in J Allergy Clin Immunol 2002, 109 (Suppl 2), 447-460 reported that distal lung diseases appear to increase the risk of recurrent asthma exacerbation, while disease-related anatomic changes in the small airways of the distal lung are prominent in fatal asthma. In this respect, in his opinion, the administration of drug with particles of a diameter of about 1 micron (referred as "extrafine" aerosols) could be advantageous. The clinical significance of distal lung disease makes this region an important therapeutic target so particles able to reach and deposit into such region could better contribute to the management of the disease. It has been also reported that, among the particles smaller than 0.5 micron, those with a diameter less or equal than 0.3 micron, preferably between 5 and 300 nm, can be deposited in the alveolar region of the lung by sedimentation. This range of particle has been referred to in the literature as "ultrafine" particles.

"Ultrafine" particles generated from di-2-ethylhexyl sebacate (DEHS) as a model, have also been reported to have a good airway penetration (Anderson P et al Chest 1990, 97, 1115-1120). Therefore medicinal aerosol particles having a diameter <0.1 µm can be particularly effective in case of airway obstruction in asthmatic subjects wherein the pathology is associated with mucus ipersecretion which hinders the diffusion of the drug or in patients affected by obstructive lung diseases such as COPD. Intuitively indeed, one would expect the reduction in the lumen of airways by mucus and permanent constriction would require finer clouds for perfusion.

In virtue of the inherent anti-inflammatory properties of LABAs, relevant formulations capable of delivering a significant fraction of fine particles would be expected to be of great advantage in patients affected by broncho-pulmonary obstructive diseases. Amirav I et al in J Nucl Med 2002, 43, 487-491 emphasize the need for improvement in aerosol delivery by targeting narrow peripheral airways with superfine aerosols in the treatment of inflammation airways diseases and in particular in acute bronchiolitis.

Salmeterol is a selective $\beta_2$-receptor agonist, exerting, upon inhalation, a prolonged bronchodilation up to 12 hours. It is currently marketed as a CFC suspension formulation (Serevent®).

In view of the above considerations, it would be highly advantageous to provide highly efficient salmeterol formulations to be administered by pMDI characterized by a deeper lung penetration and better performance than that of the formulation currently on the market.

DESCRIPTION OF THE INVENTION

The object of the present invention is to provide a pharmaceutical aerosol solution formulation to be administered by pMDI, having a suitable shelf-life for pharmaceutical use, comprising salmeterol as active ingredient, a HFA propellant, a suitable amount of co-solvent and optionally a proper amount of water wherein the active ingredient is completely dissolved in the propellant-cosolvent system. Said solution is able to provide on actuation of the formulation, a fraction of particles equal to or less than 1.1 micron of at least 30% as defined by the content stages S6-AF of an Andersen Cascade Impactor relative to the total amount of the fine particle dose collected in the stages S3-AF of the impactor.

The formulation of the invention is able to deliver a significant fraction of particles having a diameter equal or less than 1.1 micron, comprising both extrafine particles, according to the definition of Martin R in J Allergy Clin Immunol 2002, 109 (Suppl 2), 447-460 and particles having a diameter equal or less than 0.3 micron (ultrafine particles, according to the definition of other authors). By virtue of these characteristics the formulation of the invention will be hereinafter referred to as superfine formulation.

In the prior art sub-micron aerosol formulations (including HFA formulations) have only been reported as microemulsions containing surface active agents such as lecithin (WO 01/78689, WO 00/27363; Dickinson P et al J Drug Target 2001, 9, 295-302).

In the description, except where otherwise indicated, drug quantities are given as appropriate for salmeterol base but it will be understood that for a salmeterol xinafoate or another pharmaceutically acceptable salt thereof an appropriate conversion to give a suitable weight of active principle in the delivered dose may be made. For example a dose of 25 µg of salmeterol equates to a dose of 36.3 µg of salmeterol xinafoate. As a preferred aspect of the present invention, we provide a pharmaceutical aerosol formulation comprising 0.005-0.15%, preferably 0.01-0.10%, more preferably 0.02-0.05% w/v salmeterol or one of its pharmaceutically acceptable salts such as xinafoate as active ingredient in solution in a liquefied HFA propellant and a co-solvent preferably selected from a pharmaceutically acceptable alcohol, characterized in that the fraction of particles equal to or less than 1.1 micron is higher or of at least 30%. The formulations may also contain water in an amount up to 5% w/w of the total weight of the formulation, preferably from 0.5 to 5%, more preferably from 1 to 3% w/w, being 2% w/w the most preferred one.

It has indeed been found that a proper amount of water can favourably affect the solubility of the active ingredient in the HFA:cosolvent mixtures so allowing to reduce the amount of the cosolvent. In fact, it is well known that by increasing the amount of the cosolvent, the respirable fraction or fine particle fraction (i.e. the ratio between the fine particle dose and the dose delivered from the actuator) decreases.

As a further particular aspect of the invention we provide formulations comprising 0.02-0.05% w/v salmeterol or one of its pharmaceutically acceptable salt such as xinafoate as active ingredient in solution in a liquefied HFA propellant, a co-solvent selected from the pharmaceutically acceptable alcohols and a proper amount of water, characterized in that the fraction of particles less than 1.1 micron is higher than or equal to 30% as defined by the content of stages S6-AF of an Andersen Cascade Impactor relative to the fine particle dose.

Advantageously the pH of the formulation is adjusted to be between 2.5 and 5.0 as determined in the model vehicle system reported in EP 1157689. The pH will be preferably adjusted by adding the proper amount of an inorganic acid, preferably selected from hydrochloric, hydrobromic, nitric or phosphoric acid, preferably hydrochloric acid.

In the prior art HFA solution formulations of $\beta_2$-agonists for aerosol delivery through pressurized metered-dose inhalers have been disclosed.

WO 94/13262 in the name of Boehringer Ingelheim provides aerosol solution formulations comprising a medicament, an HFC propellant, a cosolvent and an inorganic or an organic acid as a stabiliser for preventing the chemical degradation of the active ingredient. Most examples relate to ipratropium bromide, an anticholinergic drug. As far as $\beta_2$-agonists are concerned, only formulations containing fenoterol, a short acting derivative not chemically related to salmeterol are exemplified. As far as the water content is concerned, in the application it is stated that a small amount of water (up to about 5% by weight) may also be present in the propellant/cosolvent system. In the case of ipratropium bromide, it is reported that addition of 1% water reduces the decomposition due to dehydration. The document is silent about the effects of water on $\beta_2$-agonists.

WO 98/34596 in the name of 3 M refers to solution formulations containing a propellant and a physiologically acceptable polymer which could help the solubilisation and the stability as well of the active ingredients.

WO 98/34595 in the name of Jago Research refers to aerosol formulations in the form of solutions or suspensions in which the propellant is a mixture of a HFA and carbon dioxide. The presence of carbon dioxide can improve either physical and chemical stability of active compounds. Salmeterol is cited among the active compounds which can be used but no examples are reported.

WO 00/06121 in the name of Jago Research refers to propellant mixtures for aerosol containing dinitrogen monoxide and a hydrofluroalkane in the preparation of suspension and solution aerosols. The use of dinitrogen monoxide may improve the stability during storage of oxidation-sensitive active ingredients. As far as LABAs such as formoterol fumarate and salmeterol xinafoate, only examples referred to suspensions are reported.

In WO 98/56349 the applicant described solution compositions for use in an aerosol inhaler, comprising an active material, a propellant containing a hydrofluroalkane (HFA), a co-solvent and further comprising a low volatility component to increase the mass median aerodynamic diameter (MMAD) of the aerosol particles on actuation of the inhaler. In some cases a small quantity of water may be added to the composition to improve the solution of the active material and/or the low volatility component in the cosolvent.

WO 01/37805 in the name of Glaxo regards pharmaceutical aerosol formulations comprising salmeterol or a pharmaceutically acceptable salt thereof in a solution of a HFA propellant, a solubilizing agent such as ethanol and a low volatility component to increase the MMAD of the aerosol particles on actuation of the inhaler as determined by the content of stages 3-5 of an ACI. For a concentration of salmeterol (present as xinafoate) of around 0.04% in HFA 134a, an amount of ethanol of 35-38% w/w, especially around 37% w/w is indicated as particularly suitable. The formulations may preferably incorporate an agent in an amount capable of preventing chemical degradation of salmeterol, e.g. bases such as sodium or potassium hydroxide or sodium carbonate or an organic amine. It may be necessary also to incorporate a small quantity of water into the formulation e.g. 0.05-2% w/w water or more preferably 0.1-1% w/w water.

In the examples, solutions of salmeterol in HFA and ethanol without low volatility components are only reported as reference formulations. There is no water in these formulations and the amount of ethanol is 37% w/w.

The technical problem in WO 01/37805 is to match the particle size distribution of the suspension formulations containing CFC propellant, on the market. Accordingly, the formulations contain a low-volatility component in order to increase the MMAD of the aerosol particles.

According to the examples of WO 01/37805 and in particular to Example 2, when a 63 µl metering volume is used, the final concentration of salmeterol, (present as xinafoate), delivered per actuation is around 0.04% w/v and the propellant is 1,1,1,2-tetrafluoroethane, an amount of ethanol of 24% w/w, in presence of 1.3% w/w of glycerol, is required.

In Table 1 solution aerosols containing 37% ethanol or 37% ethanol and 1% glycerol actuated by a metering valve having a 63 µl metering chamber, and tested with a 0.22 mm actuator are compared.

The percentage of Fine Particle Mass (FPM) that is the sum of the drug amount collected from stages 5 to 7 of the impactor, is 10.2% and 7.5% of the total amount, respectively.

In EP 1157689 the applicant disclosed aerosol pharmaceutical compositions comprising a $\beta_2$-agonist belonging to the class of phenylalkylamino derivatives in solution in a HFA propellant, a co-solvent whose apparent pH has been adjusted to between 2.5 and 5.0 in order to guarantee an adequate shelf-life. In a particular embodiment of the invention, isopropyl myristate (IPM) as a low-volatility component is added in order to either increase the MMAD of the aerosol particles or further improve the stability of the formulation. As far as the role of water is concerned, it is only generically stated that humidity, in the case of certain active ingredients such as formoterol, could be detrimental to the chemical stability during storage.

As mentioned above, the formulations of the invention can also comprise a further active ingredient. In particular, the addition of a corticosteroid to a long-acting $\beta_2$-agonist gives optimal control of asthma in most patients and relevant fixed combinations are increasingly used as a convenient controller in patients with persistent asthma. It has also been reported that each class of drug enhances the beneficial actions of the other. In fact, corticosteroids increase the expression of $\beta_2$-receptors and protect them against down-regulation in response to long-acting $\beta_2$-agonist exposure, whereas $\beta_2$-agonist may enhance the anti-inflammatory actions of corticosteroids (Barnes P et al. *Eur Respir J* 2002, 19, 182-191).

Accordingly, another object of the present invention is to provide highly efficient salmeterol formulations further comprising a steroid. The high fraction of superfine particles of the formulation of the invention can allow both drugs to reach the small peripheral airways region in such a way as to better exercise their synergistic effects in distal lung diseases (vide supra). Moreover, in view of the aforementioned characteristics, it might be possible to develop formulations comprising fixed combinations of salmeterol and a steroid wherein the latter one could be present in a lower dose, by maintaining the same therapeutic effect.

A further aspect of the present invention is to provide highly efficient salmeterol formulations in combination with an anticholinergic atropine-like derivative such as ipratropium bromide, oxitropium bromide and tiotropium bromide in order to provide a medicament particularly effective for the treatment of COPD.

A method of filling an aerosol inhaler with a composition of the invention is also provided, the method comprising:
  (a) preparation of a solution of one or more active ingredients in one or more co-solvents
  (b) optionally adding a proper amount of water and adjusting the pH of the solution
  (c) filling of the device with said solution
  (d) crimping with valves and gassing
  (e) adding a propellant containing a hydrofluroalkane (HFA)

A still further aspect of the invention comprises the use of the salmeterol fully dissolved in the propellant/co-solvent system and capable of providing on actuation a fraction of at least 30% of emitted particles with an aerodynamic diameter equal to or less than 1.1 microns, for the treatment of respiratory disorders such as asthma and COPD.

In view of its technical feature of providing on actuation a fraction of particles with an aerodynamic diameter of less than 1.1 micron, of at least 30%, the formulation of the invention can be particularly effective for the treatment of asthma, COPD and, generally, of airway obstruction conditions wherein the pathology is associated with mucus hyper-secretion which hinders the diffusion of the drug.

Furthermore, it may be clinically useful as a treatment to hasten the resolution of alveolar edema and of surfactant-deficiency related diseases such as acute lung injury (ALI) and acute respiratory distress syndrome (ARDS).

DETAILED DESCRIPTION OF THE INVENTION

The aerosol formulations of the invention comprise an HFA propellant and a co-solvent wherein the active ingredient is fully dissolved in such a way that the formulations are able to provide on actuation, a fraction of emitted particles of equal to or less than 1.1 microns higher or equal to 30% as defined by the content of stages S6-AF of an Andersen Cascade Impactor relative to the total fine particle dose collected in the stages S3-AF of the impactor, advantageously higher than 40%, preferably higher than 50%. Advantageously, the formulations of the invention are free of other excipients such as surfactants besides the solubilisation agent and the propellant.

Examples of HFA propellants include 1,1,1,2-tetrafluoroethane (HFA134a) and 1,1,1,2,3,3,3-heptafluoro-n-propane (HFA227) and mixtures thereof. The preferred propellant is 1,1,1,2-tetrafluoroethane (HFA134a). An alternative propellant of interest is 1,1,1,2,3,3,3-heptafluoro-n-propane (HFA227).

The co-solvent is selected from the group of lower alkyl ($C_1$-$C_4$) alcohols, polyols, polyalkylene glycols and their combinations. Other suitable co-solvents are (poly)alkoxy derivatives including polyalkoxy alcohols, [such as 2-(2-ethoxyethoxy)ethanol available under the trademark Transcutol®].

Preferably the co-solvent is an alcohol. The preferred one is ethanol. The concentration of the co-solvent (e.g. ethanol) will vary depending on the final concentration of the active ingredients in the formulation, on the presence of water and on the propellant. Preferably the amount of ethanol should not exceed around 35% w/w of the total weight of the formulation, preferably 30% w/w. When an amount of water from 0.5% to 5% w/w is present advantageously the ethanol level is between 5 and 25% w/w, preferably between 10 and 22% w/w, even more preferably between 12 and 15% w/w.

Active ingredients which may be used in the aerosol compositions of the invention are salmeterol and stereoisomers, physiologically acceptable salts, solvates and polymorphic forms thereof.

Suitable physiological salts include chloride, bromide, sulphate, phosphate, maleate, fumarate, tartrate, citrate, benzoate, mesilate, ascorbate, salicylate, acetate, succinate, lactate, glutarate or gluconate. The preferred one is xinafoate.

In a particular embodiment of the invention, salmeterol may be used in the form of an enantiomerically enriched (or purified) single or R- or S-enantiomer and preferably R-salmeterol may desirably be employed.

Said active ingredient can be used alone or in combination with steroids such as beclometasone dipropionate (BDP), flunisolide, mometasone furoate, fluticasone propionate, ciclesonide, budesonide and its 22R-epimer, with anticholinergic atropine-like derivatives such as ipratropium bromide, oxitropium bromide, tiotropium bromide or with drugs useful for the management of respiratory diseases such as methylxanthines, anti-leukotrienes and phosphodiesterase inhibitors.

The preferred combinations concern salmeterol and fluticasone in form of propionate ester.

The concentration of salmeterol in the HFA formulation will depend on the therapeutic amount to be delivered preferably in one or two actuations.

In the foregoing drug concentrations are given as (w/v). The corresponding percentages as (w/w) can be calculated by determining the density of the vehicle.

The formulation according to the invention will be filled in a canister fitted with a suitable metering valve. We prefer that the formulation is actuated by a metering valve capable of delivering a volume of between 25 µl and 100 µl, e.g. 50 µl or 63 µl. 100 µl is also suitable.

The concentration of salmeterol will vary between 0.005 and 0.10 w/v, preferably between 0.012 and 0.050% w/v in order to deliver 12.5 or 25 µg, per actuation.

For instance, for a 25 µg dose, when a 100 µl metering volume is used, the final concentration of salmeterol delivered per actuation would be 0.025% w/v; where a 50 µl metering volume is used, the final concentration of salmeterol would be doubled, e.g. 0.050% w/v and where a 63 µl metering volume is used, which is the preferred one, the final concentration would be 0.039% w/v.

In case the adjusting of the pH turns out suitable, the apparent pH range could be between 2.5 and 5.5, preferably between 3.0 and 5.0. Strong mineral acids preferably selected from hydrochloric, nitric, phosphoric acid can be used to adjust the apparent pH.

The amount of acid to be added to reach the desired apparent pH will be pre-determined in the model vehicle reported in EP 1157689 and it will depend on the type and concentration of the active ingredient and the amount of the co-solvent. An amount of water between 0.1% and 5% w/w, preferably between 1 and 3% w/w of the total weight of the formulation should be present. One of the formulations particularly representative of the invention contains salmeterol (as xinafoate) 0.04% w/v (based on weight of salmeterol base), ethanol 15% w/w, water 2% w/w and HFA 134a to 100% in a can fitted with a metering valve having a 63 μl metering chamber.

The formulations of the invention will be filled into canisters suitable for delivering pharmaceutical aerosol formulations such as plastic or plastic coated glass bottle or preferably a metal can, for example an aluminium can. The formulations can also be filled in canisters having part of or all of the internal surfaces made of anodized aluminium, stainless steel or lined with an inert organic coating. Examples of preferred coatings are epoxy-phenol resins, perfluorinated polymers such as perfluoroalkoxyalkane, perfluoroalkoxyalkylene, perfluoroalkylenes such as poly-tetrafluoroethylene (Teflon), fluorinated-ethylene-propylene, polyether sulfone and a copolymer fluorinated-ethylene-propylene polyether sulfone. Other suitable coatings could be polyamide, polyimide, polyamideimide, polyphenylene sulfide or their combinations.

To further improve the stability, cans having a rim with rounded edges, preferably a rolled neck or rolled-in rim, a part or full rollover rim can be used according to the teaching of the co-pending application n. WO 02/72448.

The canister is closed with a metering valve. The metering valves are designed to deliver a metered amount of the formulation per actuation and incorporate a gasket to prevent leakage of propellant through the valve.

The gasket may comprise any suitable elastomeric material such as for example low density polyethylene, chlorobutyl, black and white butadiene-acrylonitrile rubbers, butyl rubber, neoprene, EPDM (a polymer of ethylenepropylenediene monomer) and TPE (thermoplastic elastomer). EPDM and TPE rubbers are preferred. EPDM rubbers are particularly preferred. Suitable valves are commercially available from manufacturers well known in the aerosol industry, for example, from Valois, France (eg. DF10, DF30, DF60), Bespak plc, UK (eg. BK300, BK356, BK357) and 3M-Neotechnic Ltd, UK (eg. Spraymiser). The DF31 valve of Valois, France is also suitable. Valve seals, especially the gasket seal, and also the seals around the metering chamber, will preferably be manufactured of a material which is inert to and resists extraction into the contents of the formulation, especially when the contents include ethanol.

Valve materials, especially the material of manufacture of the metering chamber, will preferably be manufactured of a material which is inert to and resists distortion by contents of the formulation, especially when the contents include ethanol. Particularly suitable materials for use in manufacture of the metering chamber include polyesters eg polybutyleneterephthalate (PBT) and acetals, especially PBT.

Materials of manufacture of the metering chamber and/or the valve stem may be fluorinated, partially fluorinated or impregnated with fluorine containing substances in order to resist drug deposition.

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminum can to form an empty canister. The medicament is added to a charge vessel and a mixture of ethanol, water and liquefied propellant is pressure filled through the charge vessel into a manufacturing vessel. An aliquot of the formulation is then filled through the metering valve into the canister.

In an alternative process, an aliquot of the liquefied formulation is added to an open canister under conditions which are sufficiently cold that the formulation does not vaporize, and then a metering valve crimped onto the canister.

In an alternative process, an aliquot of medicament dissolved in the solubilising agent is dispensed into an empty canister, a metering valve is crimped on, and then the propellant is filled into the canister through the valve. Preferably, the processes are carried out an in inert atmosphere, for instance by insufflating nitrogen, in order to avoid the uptake of humidity from the air.

Each filled canister is conveniently fitted into a suitable channeling device prior to use to form a metered dose inhaler for administration of the medicament into the lungs of a patient. Suitable channeling devices comprise, for example a valve actuator and a cylindrical or cone-like passage through which medicament may be delivered from the filled canister via the metering valve to the mouth of a patient e.g. a mouthpiece actuator.

In a typical arrangement the valve stem is seated in a nozzle block which has an orifice leading to an expansion chamber. The expansion chamber has an exit orifice which extends into the mouthpiece. Actuator (exit) orifice diameters in the range 0.15-0.45 mm especially 0.2-0.45 mm are generally suitable e.g. 0.25, 0.30, 0.33 or 0.42 mm. 0.22 mm is also suitable. For certain formulations, in particular in case the percent amount of ethanol exceed 22 to 25% w/w on the weight of the formulation, it would be useful to utilize laser-drilled actuator orifices having a diameter ranging from 0.10 to 0.22 mm, in particular from 0.12 to 0.18 mm as those described in the co-pending application n. EP 1130521.6.

The use of such fine orifices also increases the duration of cloud generation and lowers its velocity. These changes facilitate the coordination of cloud generation with the slow inspiration of the patient.

The aerodynamic particle size distribution of each tested formulation of the invention can be characterized using a Multistage Cascade Impactor according to the procedure described in European Pharmacopoeia $2^{nd}$ edition, 1995, part V.5.9.1, pages 15-17. In this specific case, an Andersen Cascade Impactor (ACI) was utilized operating at a flow rate of 28.3 l/min. Deposition of the drug on each ACI plate was determined by high pressure liquid chromatography (HPLC). Mean delivered dose was calculated from the cumulative deposition in the ACI. Mean respirable dose (fine particle dose) was obtained from the deposition on Stages 3 (S3) to filter (AF) (S3-AF) corresponding to particles ≦4.7 microns, divided by the number of actuation per experiment, while mean "superfine" dose was obtained from the deposition on Stages 6 to filter (S6-AF) corresponding to particles ≦1.1 microns.

ACI apparatus was also utilized to determine the percent amount of Fine Particle Mass (FPM) represented by the sum of drug collected from Stages 3 to 5 and Stages 5 to 7 of the impactor, respectively, with respect to the total mass collected in the impactor plus device and throat. It has been so demonstrated that by delivering the solution formulation of the invention a FPM (S5+S6+S7) percent of at least 12.00% is provided.

Administration of the formulations of the invention may be indicated for the treatment of mild, moderate or severe, acute or chronic symptoms or for prophylactic treatment of respiratory diseases such as asthma and chronic obstructive pulmonary disease (COPD). Other respiratory disorders characterized by obstruction of the peripheral airways as a result of inflammation and presence of mucus such as chronic obstructive bronchiolitis and chronic bronchitis can also benefit from this kind of formulation.

The invention is illustrated with reference to the following examples.

Example 1

Superfine Salmeterol HFA Formulation

A formulation was prepared with the following composition:

| | | |
|---|---|---|
| Salmeterol (as xinafoate) | 0.04% w/v | (based on weight of salmeterol Base) (36.25 µg/63 µl) |
| Ethanol | 15% w/w | |
| Water | 2% w/w | |
| HCl 1M | 10 mg/cans | |
| HFA 134a | to 100% | |

The formulation (120 actuations/canister, overage of 40 actuations) was filled into inert coated aluminium cans (two stage pressure filling) under pressure and fitted with a metering valve having a 63 µl metering chamber. Two actuators were used: 0.22 and 0.30 mm. Results were obtained as a mean of 2 cans performing 20 actuations for each can.

The aerodynamic particle size distribution was determined by ACI, according to the description on page 16 lines 16-24.

The delivery characteristics of the formulation are reported in Table 1. In particular the following parameters are reported: i) nominal dose: theoretical dose per single actuation; ii) delivered dose: amount of active particles deposited into the all ACI stages; iii) respirable dose (fine particle dose): amount of active particles of size equal to or less than 4.7 microns (S3-AF); iv) respirable fraction (fine particle fraction): ratio between the respirable dose and the delivered dose; v) "superfine" dose: amount of active particles equal to or less than 1.1 microns (S6-AF); vi) "superfine" fraction: ratio between the "superfine" dose and the respirable dose.

orifice diameters are respectively 15.41% and 8.36% of the total mass ex-valve (i.e. mass collected in the impactor+device+throat).

The percent amount of fine particle mass collected from stage 5 to stage 7 (S5+S6+S7) delivered from actuators of 0.22 mm and 0.30 mm orifice diameters are respectively 27.86% and 13.92 of the total mass ex-valve.

In conclusion, the formulation of the invention gives rise to a significantly higher fraction of respirable particles than the formulations of the prior art.

The invention claimed is:

1. A pharmaceutical aerosol formulation to be administered by a pressurized metered dose inhaler, which consists of:
   salmeterol, a stereoisomer thereof, or a physiologically acceptable salt thereof, and optionally a corticosteroid, or an anticholinergic compound, in solution in a propellant system, said propellant system consisting of a liquefied HFA propellant, a co-solvent, a mineral acid and between 1 and 3% w/w water,
   wherein said cosolvent is present in an amount which is no more than 35% w/w based on the total weight of said formulation, and
   wherein said formulation has a pH of 2.5 to 5.5, and
   wherein said pH of said formulation has been adjusted by addition of said mineral acid.

2. A pharmaceutical formulation according to claim 1, which contains, as said cosolvent, at least one member selected from the group consisting of a lower alkyl (C1-C4) alcohol, a polyol, a polyalkylene glycol, a (poly)alkoxy alcohol, and mixtures thereof.

3. A pharmaceutical formulation according to claim 2, which contains ethanol.

4. A pharmaceutical formulation according to claim 3, wherein said ethanol is present in an amount of no more than 25% w/w.

5. A pharmaceutical formulation according to claim 1, wherein said water is present in an amount between 1 and 2% w/w.

6. A pharmaceutical formulation according to claim 1, wherein a fraction of particles equal to or less than 1.1 µm delivered on actuation of an inhaler, which contains said formulation, is higher than or equal to 30% as defined by the content of the stages S6-AF of an Andersen Cascade Impac-

TABLE 1

Delivery characteristics of the salmeterol HFA solution formulations of the Ex. 1.

| | Nominal dose (µg) | Delivered dose (µg) * | Respirable dose (µg) * | Respirable fraction (%) | Superfine dose (S6-AF) (µg) * | Superfine Fraction (%) |
|---|---|---|---|---|---|---|
| Formulation Ex 1 Act diam 0.22 mm | 25 | 34.49 | 14.51 | 42.08 | 8.70 | 59.9 |
| Formulation Ex 1 Act diam 0.30 mm | 25 | 33.55 | 8.17 | 24.35 | 5.06 | 61.9 |

* as xinafoate

The results show that the formulations of the invention give rise upon actuation to a very high percentage of particles with a diameter equal or less than 1.1 microns The percent amount of fine particle mass collected from stage 3 to stage 5 (S3+S4+S5) delivered from actuators of 0.22 mm and 0.30 mm tor, relative to the content of the stages S3-AF of an Andersen Cascade Impactor.

7. A pharmaceutical formulation according to claim 6, wherein said fraction of particles equal to or less than 1.1 µm delivered on actuation of said inhaler is higher than 40%.

8. A pharmaceutical formulation according to claim 1, wherein said physiologically acceptable salt of salmeterol is salmeterol xinafoate.

9. A pharmaceutical formulation according to claim 8, wherein salmeterol xinafoate is present in a concentration of 0.005 to 0.15% w/v.

10. A pharmaceutical formulation according to claim 1, which contains one or more hydrofluoroalkanes selected from the group consisting of HFA 134a, HFA 227, and mixtures thereof.

11. A pharmaceutical formulation according to claim 1, wherein the concentration of salmeterol is 0.04% w/v, the concentration of ethanol is 15% w/w, and the concentration of water is 2% w/w.

12. A pharmaceutical formulation according to claim 1, filled in a canister having part or all of its internal metallic surfaces made of standard aluminium, stainless steel, anodized aluminium or lined with an inert organic coating.

13. A pharmaceutical formulation according to claim 1, wherein said anticholinergic compound is ipratropium bromide, oxitropium bromide or tiotropium bromide.

14. A pharmaceutical formulation according to claim 1, in which said corticosteroid is present.

15. A pharmaceutical formulation according to claim 1, in which said anticholinergic compound is present.

16. A pharmaceutical formulation according to claim 1, wherein said water is present in an amount of between 1% and 2% w/w.

17. A pharmaceutical formulation according to claim 1, wherein said water is present in an amount of between 2% and 3% w/w.

18. A pharmaceutical formulation according to claim 1, wherein said water is present in an amount of 2% w/w.

19. A pharmaceutical formulation according to claim 1, which consists of:
   salmeterol, a stereoisomer thereof, or a physiologically acceptable salt thereof, in solution in a propellant system, said propellant system consisting of a liquefied HFA propellant, a co-solvent, a mineral acid and 1 and 3% w/w water.

20. A pharmaceutical formulation according to claim 1 which consists of: salmeterol, a stereoisomer thereof, or a physiologically acceptable salt thereof, and a corticosteroid, in solution in a propellant system, said propellant system consisting of a liquefied HFA propellant, a co-solvent, a mineral acid and between 1 and 3% w/w water.

21. A pharmaceutical formulation according to claim 1, which consists of: salmeterol, a stereoisomer thereof, or a physiologically acceptable salt thereof, and an anticholinergic compound, in solution in a propellant system, said propellant system consisting of a liquefied HFA propellant, a co-solvent, a mineral acid and between 1 and 3% w/w water.

22. A method of preparing a pharmaceutical formulation according to claim 1, said method comprising:
   (a) preparing a solution of salmeterol, a stereoisomer thereof, or a physiologically acceptable salt thereof, and optionally a corticosteroid or an anticholinergic compound, in one or more co-solvents;
   (b) adjusting the pH of said formulation to 2.5 to 5.5 by addition of a mineral acid;
   (c) optionally adding between 1 and 3% w/w of water;
   (d) filling a device with said solution;
   (e) crimping said device with a valve and gassing; and
   (f) adding a said propellant.

23. A method according to claim 22, wherein said device is provided with a valve actuator whose orifice diameter is 0.22 mm.

24. A method for the treatment of a respiratory disease selected from the group consisting of chronic obstructive pulmonary disease, asthma, a disease due to obstruction of peripheral airways as a result of inflammation or mucus hypersecretion, pulmonary edema or a surfactant-deficiency related disorder, acute lung injury or acute respiratory distress syndrome, comprising administering an effective amount of a pharmaceutical formulation according to claim 1 to a subject in need thereof.

25. A method according to claim 24, wherein said respiratory disease is asthma or chronic obstructive pulmonary disease.

26. A method according to claim 25, wherein said respiratory disease is due to obstruction of peripheral airways as a result of inflammation or mucus hypersecretion.

27. A method according to claim 24, wherein said respiratory disease is pulmonary edema or a surfactant-deficiency related disorder.

28. A method according to claim 24, wherein said respiratory disease is acute lung injury or acute respiratory distress syndrome.

29. A method for the treatment of a asthma, comprising administering an effective amount of a pharmaceutical formulation according to claim 14 to a subject in need thereof.

30. A method for the treatment of a chronic obstructive pulmonary disease, comprising administering an effective amount of a pharmaceutical formulation according to claim 15 to a subject in need thereof.

* * * * *